United States Patent [19]

McMahon

[11] Patent Number: 6,054,317
[45] Date of Patent: Apr. 25, 2000

[54] SYSTEM FOR THE CELL CULTURE AND CRYOPRESERVATION OF MARINE INVERTEBRATES

[76] Inventor: Peter McMahon, 5380 Los Robles Dr., Carlsbad, Calif. 92008

[21] Appl. No.: 08/846,367

[22] Filed: Apr. 30, 1997

Related U.S. Application Data

[63] Continuation-in-part of application No. 08/562,023, Nov. 22, 1995, abandoned.

[51] Int. Cl.⁷ ..................................................... C12N 5/06
[52] U.S. Cl. ......................... 435/404; 435/325; 435/347; 435/405; 435/406; 435/408
[58] Field of Search ..................................... 435/325, 347, 435/404, 405, 406, 408

[56] References Cited

U.S. PATENT DOCUMENTS

| | | | |
|---|---|---|---|
| 3,623,455 | 11/1971 | Euclid et al. | 119/231 |
| 4,449,480 | 5/1984 | Ison et al. | 119/236 |

FOREIGN PATENT DOCUMENTS

| | | |
|---|---|---|
| 0253817 | 9/1994 | Japan . |
| 9314192 | 7/1993 | United Kingdom . |

OTHER PUBLICATIONS

Engvall et al., J. Cell Biology 102: 708–710 (1986).
Minoura et al., Biochem. Biophys. Res. Communications 208(2): 511–516 (1995).
Bayne, Advances in Cell Culture, Academic Press, vol. 1, 1981, 297–334.
Hay, Animal Cell Culture: A Practical Approach, Oxford/IRL Press Ltd., 1986, 73–76.

*Primary Examiner*—Jean C. Witz
*Attorney, Agent, or Firm*—James C. Weseman; The Law Offices of James C. Weseman

[57] ABSTRACT

A system for the culture of eukaryotic cells of marine invertebrates employing a culture medium containing a mixture of sodium, magnesium, chlorine, potassium, calcium, bromine, and sulfate is disclosed, as well as a system for the cryopreservation of such cells in which the medium contains dimethyl sulfoxide.

12 Claims, 2 Drawing Sheets

SYSTEM FOR THE CELL CULTURE AND CRYOPRESERVATION OF MARINE INVERTEBRATES

RELATED APPLICATION DATA

This application is a continuation-in-part of commonly-owned U.S. patent application Ser. No. 08/562,023, filed Nov. 22, 1995 now abandoned.

TECHNICAL FIELD

The present invention relates to marine cell culture, and, more particularly, to a system for the in vitro culture and cryopreservation of marine invertebrate cells.

BACKGROUND OF THE INVENTION

A number of synthetic basal media have been developed for animal cell culture, especially for mammalian and insect cells. Commercially available media include: Eagle media, M 199, Dulbecco's modified Eagle's medium (DME), Ham's F10 and F12, RPMI 1640, Grace's Insect media and Leibovitz L15. These media, in conjunction with bovine serum or specific growth factors, are often sufficient to support animal cell growth. The formulation of these media, however, are insufficient for sustained growth and proliferation of marine invertebrate cells.

Historically, there has been no flexible basal nutrient media available which can support the in vitro proliferation or preservation of cells from a diverse number of multicellular, eukaryotic, marine invertebrate species.

Recent advances in cellular biology have demonstrated the importance of the synergistic involvement of a variety of media components, including ions, nutrients, growth factors and attachment matrices in the development and proliferation of higher eukaryotic cells.

The inorganic salts in culture media have two major functions. First, salt concentrations are created to approach the natural salt concentration levels in the environment from which the cells are derived. This will minimize any deviation in osmotic pressure on the cells that would require energy consuming ionic pumps to maintain cellular integrity.

Secondly, these salts include many ions which are utilized as enzymatic cofactors and intracellular messengers. Often, for ions to be effectively transported into the cell, additional carrier molecules are needed in the medium. In mammalian systems, transferrin is a carrier of iron. In marine invertebrate systems, it has been demonstrated that metal chelators like diethylenetetramine pentaacetic acid ("DTPA"), citrate and amino acids (lysine and taurine) help to transport metal ions into molluscan tissue. See Coombs, T. C. (1977) *Proc. Anal. Div. Chem. Soc.* 14:219.

Although most mammalian culture media utilize glucose as the main carbon source, others have demonstrated the benefits of alternative carbon sources for invertebrate culture. See Grace, T. D. C. (1962) *Nature* 195:788–789, and Leibovitz, A. (1983) *Am J. Hyg.* 78:173–180.

It is known that many animal cells grow best when attached to natural substrates like collagen, laminin, and fibronectin. It has been shown that the addition of ascorbic acid to culture medium increased the production and deposition of collagen by mammalian cells. See Engvall, E., et al (1986) *J. Cell Biol.* 102:703–710. The production of collagen by cells in culture helps to create a natural matrix for growth. This type of matrix is very important for many marine invertebrate cells. Sponges, for example, are mostly cells on a collagen mesh.

In a general basal media it is very difficult to define all the requirements animal cells need for growth. The use of bovine or fetal bovine serum as a supplement, as used in mammalian culture systems, does not work with marine invertebrate cells. Serum or hemolymph from marine gastropods, such as *Haliotis sp.* and *Strombus sp.*, offer an alternative and effective source of additional lipids, trace metals, growth factors and nutrients. These improve the cultured growth of marine invertebrates.

The preservation of cultured cells and a method for preserving and shipping field samples of marine invertebrates offer both economical and environmental savings by reducing or eliminating large scale re-collections of organisms of interest. Serman, J. K. (1964) *Proc. Soc. Exptl. Biol. Med.* 117:251–264 discloses the value of adding dimethyl sulfoxide (DMSO) to medium in order to prevent ice crystals from rupturing cells during freezing.

Accordingly, it is an object of the present invention to provide a system which employs a basal nutrient medium which is designed to facilitate the in vitro growth, proliferation, and cryopreservation of multicellular, marine invertebrate cells.

It is another object of the present invention to provide a system that will accommodate a wide variety of species and cell types, rather than optimize for any single specific cell line.

It is a further object of the present invention to provide a system employing media that is reliable, convenient to use, and cost effective in its manufacture.

DISCLOSURE OF THE INVENTION

The present invention provides a system for the proliferation of marine invertebrate cells in in vitro culture, and the production of cell metabolites therefrom.

In one aspect, the present system comprises a culture of viable eukaryotic cells or tissue derived from at least one marine invertebrate organism in association with a culture medium which comprises components in the following approximate ranges: From 7.875 to 13.125 g/L of sodium, from 1.0 to 1.69 g/L of magnesium, from 14.25 to 23.8 g/L of chlorine, from 0.29 to 0.48 g/L of potassium, from 0.3 to 0.5 g/L of calcium, from 0.0225 to 0.0375 g/L of bromine and from 2.0 to 3.38 g/L of sulfate.

Another embodiment of the culture medium of the present system includes carbon sources, in which the carbon sources are selected from the group consisting of galactose, mannose and fructose. Further embodiments of the media include from approximately 30 to 300 mg/L of taurine, and from approximately 10 to 100 mg/L of ascorbic acid. The culture media may also comprise from approximately 3 to 20% by volume gastropod plasma or components fractionated therefrom.

A further aspect of the invention provides a method for employing the present system to produce desirable metabolites from the cells established in culture.

A still further aspect of the invention includes the present system in which propagating cells are attached to microcarriers, such as of polystyrene.

In yet another aspect of the invention, a system is provided for the cryopreservation of cultured cells and tissue from marine invertebrates. In this aspect, the system comprises a culture of viable eukaryotic cells or tissue derived from at least one marine invertebrate organism in association with the present culture medium to which has been added components in the following approximate ranges:

From 5 to 20% by volume gastropod plasma and about 7.5% by volume dimethyl sulfoxide.

The novel features of this invention, as well as the invention itself, both as to its structure and operation, will be best understood from the accompanying drawings taken in conjunction with the accompanying description.

DETAILED DESCRIPTION OF THE INVENTION

Figure 1:
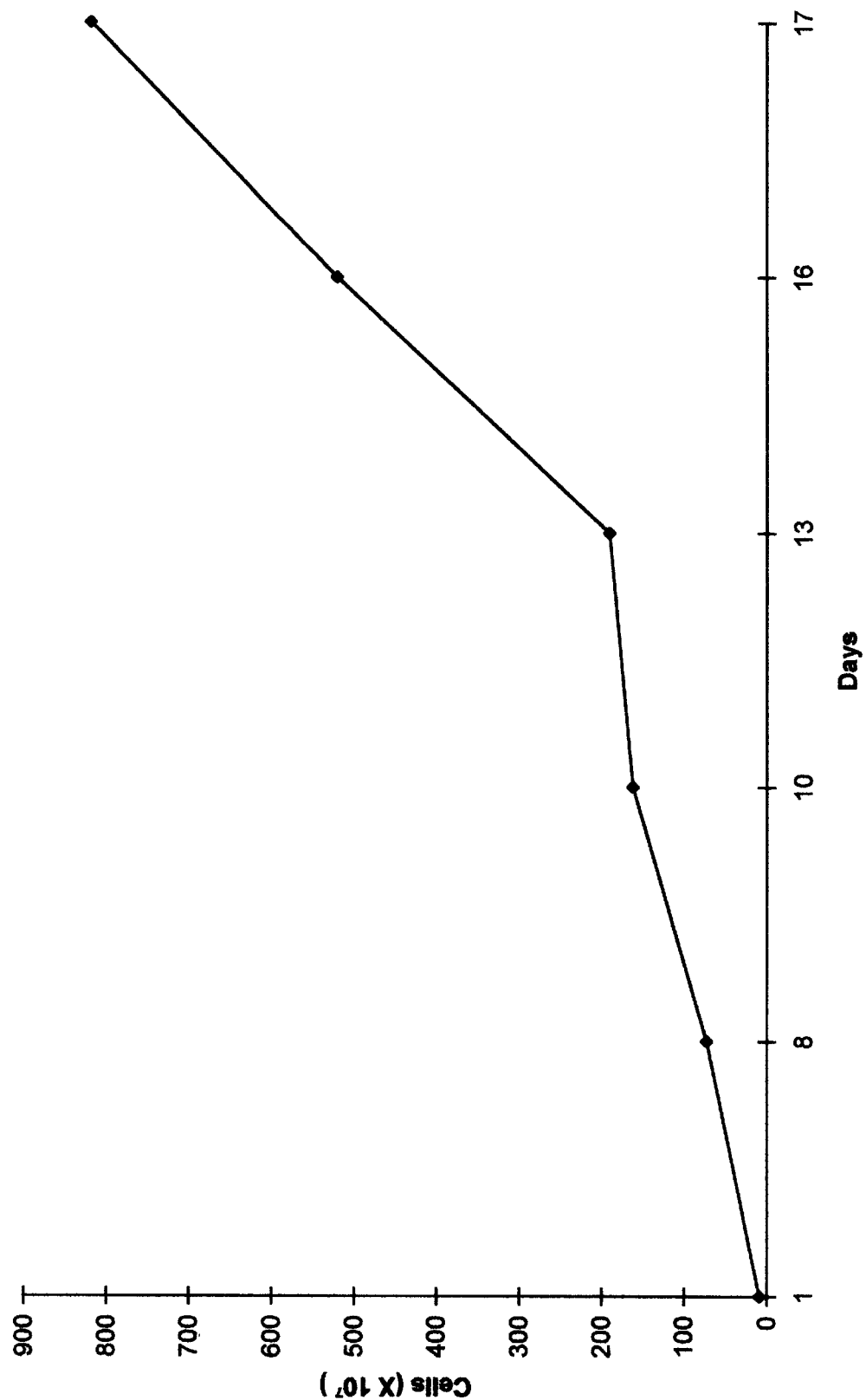
FIG. 1 depicts a growth curve of *Aplysina fistularis* in a suspension culture using a medium in accordance with the present invention which includes polystyrene microcarriers as described in Example 3.

The present invention provides a system for the proliferation of marine invertebrate cells in in vitro culture, and the production of cell metabolites therefrom.

In one aspect, the present system comprises a culture of viable eukaryotic cells or tissue derived from at least one marine invertebrate organism in association with a culture medium which comprises components in the following approximate ranges: From 7.875 to 13.125 g/L of sodium, from 1.0 to 1.69 g/L of magnesium, from 14.25 to 23.8 g/L of chlorine, from 0.29 to 0.48 g/L of potassium, from 0.3 to 0.5 g/L of calcium, from 0.0225 to 0.0375 g/L of bromine and from 2.0 to 3.38 g/L of sulfate.

A further embodiment of the culture medium of the present system includes carbon sources, in which the carbon sources are selected from the group consisting of galactose, mannose and fructose. Further embodiments of the media include from approximately 30 to 300 mg/L of taurine, and from approximately 10 to 100 mg/L of ascorbic acid. The culture media may also comprise from approximately 3 to 20% by volume gastropod plasma or components fractionated therefrom.

A further aspect of the invention includes the present system in which propagating cells are attached to microcarriers, such as beads made of polystyrene. This aspect of the invention facilitates the transfer of marine invertebrate cell cultures from low volume plasticware to larger suspension systems to permit larger volume production of the cell cultures, or the metabolites derived therefrom. The utilization of plastic microcarriers also allows the direct transfer of attached cells to a flask or bioreactor.

In another aspect of the invention, a system is provided for the cryopreservation of cultured cells and whole pieces of tissue obtained from marine invertebrates. In this aspect, the system comprises a culture of viable eukaryotic cells or tissue derived from at least one marine invertebrate organism in association with the present culture medium to which has been added components in the following approximate ranges: From 5 to 20% by volume gastropod plasma and about 7.5% by volume dimethyl sulfoxide (DMSO).

The basal medium employed in the present system is a new formulation of nutrients, salts and other components which make possible the growth, proliferation and cryopreservation of multicellular marine invertebrate cells. The medium contains balance amounts of amino acids, carbohydrates, vitamins, ions and other components, which allow its flexible use in growing a large variety of marine invertebrates. This is a basal medium designed to effectively culture a wide variety of proliferating cell and tissue cultures. This invention is particularly, though not exclusively, useful for generating a medium to store frozen field or culture samples in a viable state, eliminating the need for expensive and ecologically destructive re-collection of rare sample organisms.

This invention defines such media which can be used to produce biomass for the study and production of metabolites and other natural products from a genetically diverse array of marine species, such as but not limited to porifera, gastropods, and tunicates.

It is the balance of these parameters, with specific focus on the requirements of multicellular marine invertebrates, that is the essence of this invention. Key elements provided in this medium for the culture of marine invertebrate cells are derived from the state-of-the-art correlation that animal cells have certain ionic, nutrient, matrix protein attachment and growth factors. These elements are related to the requirements for growth and development.

The basal nutrient medium in this invention is designed to facilitate the in vitro growth, proliferation and cryopreservation of multicellular, marine invertebrate cells. This is intended to be a general medium that will accommodate a wide variety of species and cell types. The invention recognizes major inorganic ions be adjusted to concentrations approaching that of their natural marine environment. See Hughs, K. D. (1993) *Analytical Chem.* 65(20):888–889. In addition, the invention includes metal binding agents, such as taurine, to aid in the transport of important ions into the cells.

Moreover, the invention recognizes that carbon sources in addition to glucose, such as mannose, fructose and galactose, can be utilized as alternative energy sources in certain invertebrates. Still another feature of the invention is the addition of ascorbic acid as an anti-oxidant and rate limiting cofactor of collagen production. The invention also recognizes the desirability of supplements, and in particular the use of gastropod hemolymph, plasma or serum, most usually plasma (the cell free hemolymph or blood), from marine gastropods, including but not limited to *Haliotis sp.* and *Strombus sp.*

An additional advantage provided by the present invention is a system for freezing and storing viable field and culture samples of marine invertebrates. This is accomplished by the use of the media containing gastropod plasma and DMSO, as further described below.

A number of commercially available synthetic media can serve as the base starting point for the final media formulations of this invention. Each of the following commercially-available media are known to function in the present system, after being adjusted to the disclosed formulation requirements of the invention, although a range of performance is to be expected: Eagle, DME, M 199, Ham's F10, F12, RPMI 1640 and Leibovitz L15. The formulation which performed best is given in Table 1 and is based on RPMI 1640. Cell growth was not obtained in any of these media when used without the presently-described modifications.

Utilizing any of the above mentioned commercial media, amino acid concentrations can also be supplemented with commercially available non-essential amino acids, in particular glutamine and taurine.

Inorganic salts are added to adjust the final approximate amounts in a liter of media to be: Sodium (Na) 10.5 g, magnesium (Mg) 1.35 g, chlorine (Cl) 19.0 g, potassium (K)

0.38 g, calcium (Ca) 0.4 g, bromine (Br) 0.03 g and sulfate (SO$_4$) 2.7 g. Proper ionic balance is desirable to realize the full benefits of the invention. Because of the large number of components and flexible nature of the media, it is to be noted that these ion concentrations should lie within an approximate range of plus or minus 25% of the stated values.

In addition to the glucose (1–4.5 g/L) in the starting media, alternative sugars can be added to serve as carbon sources, desirably for example mannose at 1.44 g, fructose at 1.44 g and galactose at 4.32 g per liter of media. Again the final amount of these components should be substantially within ±25% of the above values.

Ascorbic acid is added to the media desirably at 0.05 g/L. A main goal is to improve the rate of post-translational collagen modification, and in so doing, to increase the transport of collagen out of the cell and into a matrix formation suitable to enhance cell growth.

Hemolymph is obtained from commercially-harvested 0.5–3 kg gastropods (e.g. *Haliotis sp.* or *Strombus sp.*). Known techniques for collecting hemolymph are employed to obtain serum or plasma, e.g. by arterial or venous puncture. All media containing gastropod plasma are filtered, e.g. through a standard 0.2 m filter, to remove cell contaminants. Subfractions of gastropod hemolymph, and the constituent components thereof, are obtained by known methods, such as salt precipitation, column chromatography, size exclusion (filtration, dialysis, or chromatography) or solvent extraction. Such subfractions and components are routinely screened for beneficial effects in the present system and media.

Samples of gastropod hemolymph are collected from live animals (such as *Haliotis sp.*) These samples are centrifuged at 20,000 times gravity for 30 minutes to remove the cells, and are stored at −10° to −20° C. This plasma is added to the media at levels between 3% and 20% by volume. This plasma is a desirable component of the invention in the sense that all cell types tested grew, multiplied and withstood the rigors of cryopreservation better in the presence of this plasma. The exact components in the gastropod plasma responsible for the above-mentioned advantages have not been identified. This invention recognizes, however, that selected subfractions of gastropod hemolymph will also be expected to prove beneficial and hence are considered to be included in the invention.

TABLE 1

| Compound | Amount (mg/L) | Compound | Amount (mg/L) |
|---|---|---|---|
| Salts and Buffers | | | |
| NaCl | 25,430 | KCl | 740 |
| MgSO$_4$.7 H$_2$O | 7,030 | MgCl$_2$.6 H$_2$O | 5,070 |
| CaCl$_2$ | 1,100 | Ca(NO$_3$)$_2$ | 100 |
| NaHCO3 | 2,000 | NaH$_2$PO$_4$.7 H$_2$O | 1,512 |
| NaBr | 42 | HEPES | 5,957.5 |
| Carbon Sources | | | |
| glucose | 2,000 | galactose | 4,320 |
| fructose | 1,440 | mannose | 1,440 |
| Vitamins, Amino Acids | | | |
| ascorbic acid | 50 | glutathione | 1 |
| L-arginine | 200 | L-asparagine | 1,372 |
| L-aspartic acid | 1,350 | L-cystine | 20 |
| L-glutamic acid | 1,490 | glycine | 760 |
| L-histidine | 15 | hydroxy L-proline | 20 |
| L-isoleucine | 50 | L-leucine | 50 |
| L-lysine | 40 | L-methionine | 15 |

TABLE 1-continued

| Compound | Amount (mg/L) | Compound | Amount (mg/L) |
|---|---|---|---|
| L-phenylalanine | 15 | L-proline | 1,170 |
| L-serine | 1,080 | L-threonine | 20 |
| L-tryptophan | 5 | taurine | 122 |
| L-tyrosine | 20 | L-valine | 20 |
| p-aminobenzoic | 1 | d-biotin | 0.2 |
| D-pantothenate | 0.25 | choline chloride | 3 |
| folic acid | 1 | i-inositol | 35 |
| nicotinamide | 1 | pyridoxine | 1 |
| riboflavin | 0.2 | thiamine | 1 |
| vitamine B12 | 0.005 | | |
| Haliotis sp. plasma | 10% | | |

The ability to store and ship field samples and cultures is another important attribute of this invention, since large scale re-collection of marine invertebrates is a difficult and ecologically destructive process. It is known that many of these organisms have either open or no circulation systems. This fact dictates that their tissues be relatively permeable to allow nutrient and excrement transport. It is this tissue construction that can be exploited to deliver cryopreservation solutions to the cells while they are still in "blocks" of tissue. Consequently, small pieces of tissue can be cut from these animals, placed in a medium of the invention that contains approximately 20% by volume of gastropod plasma and approximately 7.5% by volume of DMSO, and frozen slowly at −10° C. to −20° C. The DMSO protects the cells from the formation of ice crystals during freezing, and the media with the plasma protect the cell membranes during thawing. Frozen samples can be stored at −10° C. for several weeks, but long term storage will desirably be at −70° C. or below. One embodiment of the media according to the present invention is described in Table 1, containing approximately 20% gastropod plasma and approximately 7.5% DMSO.

A further embodiment of the invention is the adaptation of these marine invertebrate cell cultures from low volume plasticware to larger suspension systems. This is accomplished by allowing the propagating cells to attach to polystyrene microcarriers (Solohill Labs Inc.) which are small round spheres or beads, similar to grains of sand in appearance. Use of such microcarriers allows the direct transfer of attached cells to a stirred flask of bioreactor vessel.

The following examples serve to illustrate certain preferred embodiments and aspects of the present invention and are not to be construed as limiting the scope thereof.

EXPERIMENTAL

In the experimental disclosure which follows, all weights are given in grams (g), milligrams (mg), micrograms (µg), nanograms (ng), or picograms (pg), all amounts are given in moles (mol), millimoles (mmol), micromoles (µmol), nanomoles (nmol), picomoles (pmol), or femtomoles (fmol), all concentrations are given as percent by volume (%), proportion by volume (v:v), grams per liter (g/L), molar (M), millimolar (mM), micromolar (µM), or normal (N), all volumes are given in liters (L), milliliters (mL), or microliters (EL), and linear measurements are given in millimeters (mm), or nanometers (nm) unless otherwise indicated.

EXAMPLE 1

A specimen of the marine sponge *Haliclona sp.* is cut into strips measuring 5×5×40 mm, placed in cold freezing media containing 20% gastropod plasma and 7.5% DMSO, and then frozen at −10° C.

One month later the sample is thawed, placed in 1% sodium hyperchlorite using synthetic sea water (26.22 g/L NaClO and 1 g/L KCl)(SSW) for 60 seconds, rinsed with synthetic sea water, and passed through a metal mesh. Cells are collected by pipette and placed in medium containing 5% gastropod plasma, 0.5 mg/mL gentamicin, 1.25 µg/mL fungizone, and 0.5 mg/mL penicillin/streptomycin, for one hour at 20° C. The cells are then washed with media and placed into a plastic T75 culture flask at $1\times10^6$ cells/mL, in 15 mL of media, with 4% gastropod plasma, at 20° C. Primary cultures contained the same antifungal and antibiotic agents at 10% of the above stated levels. These agents are then diluted and washed out as the cultures are expanded.

One month later, after several generations of cell reproduction, or passages, one T75 flask is treated with 0.5 mg/mL trypsin and 0.2 mg/mL EDTA in synthetic sea water to detach the cells from the flask. These cells ($1\times10^8$) are washed in media and then split into two T75 flasks. Two days later both flasks are again harvested yielding $3.2\times10^8$ cells. These cells are placed into a 1 liter stir flask containing 100 mL of media, with 6% gastropod plasma and 5 g of polystyrene microcarriers (Solohill #104–1521). The system is allowed to incubate for two hours, stirred and then allowed to incubate for another hour. The system is then continuously stirred, with 200 mL of media containing 5% gastropod plasma being added every other day. After ten days in the stirred flask, 4.46 g of cells are recovered from the system.

The cells are extracted with methanol and then hexane. Both these extracts demonstrate antibiotic activity, similar to the natural sponge, against *Staphylococcus aureus*, in a qualitative bacterial growth bioassay.

EXAMPLE 2

Mantle epithelium tissue samples are cut from the green abalone, *Haliotis fulgens*, in strips measuring 2×5×20 mm and frozen in freezing medium at −10° C. One week later, the samples are thawed and placed in 1% sodium hyperchlorite, in synthetic sea water, for 60 seconds.

The samples are then rinsed with synthetic sea water, cut into 2×2×2 mm pieces, and placed in trypsin/EDTA/synthetic sea water for one hour, at 20° C. The cells are then passed through a metal screen and rinsed with media. The primary cultures are started in 24 well TC plastic plates, in medium plus 10% gastropod plasma, 50 µg/mL gentamicin, 0.125, µg/mL fungizone and 50 µg/mL penicillin/streptomycin, at 20° C. The samples are also split into two groups, one with 5% $CO_2$ and one in room air.

Both groups are expanded to T75 flasks and then split again after one week. At this point the cultures are allowed to become confluent. On the third passage, one month after the start of the culture, the confluent cells will began grouping into dense clusters. These epithelial cells will began to form a nucleus and thereafter deposit a hard outer wall in the shape of a circle onto the culture plastic which resembles a shell-like structure.

EXAMPLE 3

Cells ($9.3\times10^7$) from the sixth passage of the marine sponge, *Aplysina fistularis* are added to 12 g of polystyrene microcarriers and 50 mL of media without gastropod plasma. The system is allowed to incubate for one and one half hours at 20° C, and then 150 mL of media with 4.3% gastropod plasma is added with constant stirring. Every 2 to 3 days an aliquot of the culture is taken, the cell number is determined by counting on a hemocytometer, and new media is added to the system. As shown in FIG. 1, the curve reflects a plot of the total number of cells times ten million versus day in suspension culture.

After 17 days the 1 liter flask is confluent and the cell count is $8.18\times10^9$, yielding an 88-fold increase in cell number. Some of these cells are preserved in freezing medium and are later thawed to initiate new cultures.

Another aliquot of this culture, which is not treated with trypsin/EDTA, is dried onto microscope slides and run through an automated, clinical, histology system, with Masson's trichrome stain, for connective tissue. The cell clump stained with Masson's trichrome, a clinical connective tissue stain which identifies the protein collagen by a deep blue color. Thus, the slides stained positive for a large amounts of collagen, an important part of the natural sponge.

EXAMPLE 4

A marine tunicate, species unknown, is collected from Scripps Canyon in La Jolla, Calif. The specimen is cut in 2.20 mm circular slices and stored in freezing medium, at −10° C.

Three days later, one of the samples is thawed, disinfected with NaClO, antibiotics and fungicides, disrupted through a metal mesh, and then rinsed with synthetic sea water. The resulting cells are placed into 12 well tissue culture plastic plates containing medium with either 4% gastropod plasma or 10% fetal bovine plasma. The gastropod plasma wells will begin to proliferate and double their numbers after 4 days. At the same time, the cells in fetal bovine plasma will not grow and instead begin to die off. By the third passage the gastropod plasma cells are doubling every two days, so some wells are expanded to a T75 flask. The T75 cells will continue to proliferate and after another month, they are harvested and stored by cryopreservation for future use.

The cells that are left in the 12 well plates for over a month, with regular media changes, first grow to confluence and then differentiate into honeycomb structures, resembling the cross sectional slices of the original animal.

EXAMPLE 5

The tropical marine sponge, *Acanthella cavernosa* is cut into strips measuring 4×4×5 mm and stored in freezing medium at −10° C. Weeks later, samples are thawed and disinfected with NaClO, antibiotics and fungicides. The cells are then obtained by mechanical disruption through a metal screen, and put into culture at 28° C., in medium with 5% gastropod plasma.

Figure 2:
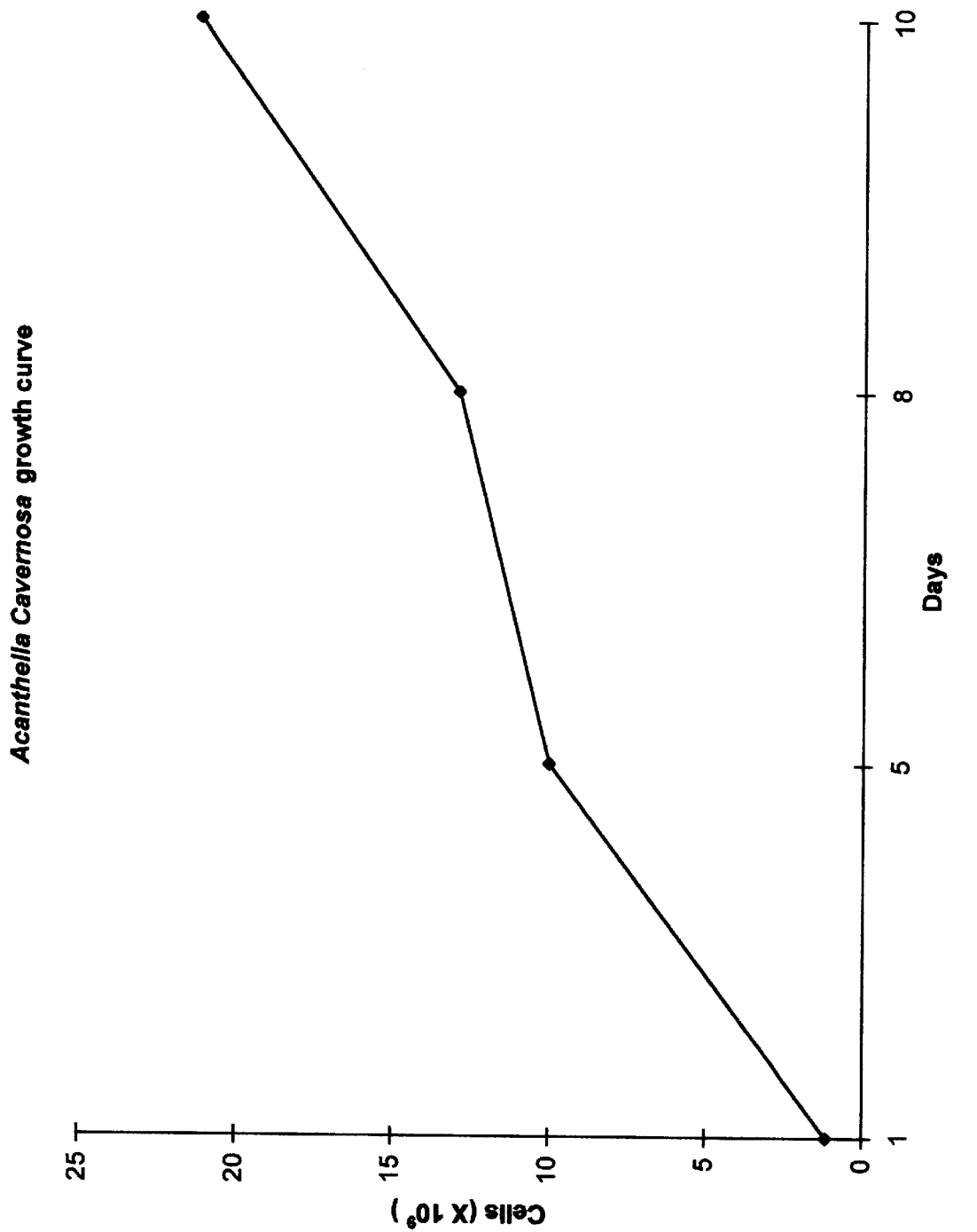
FIG. 2 depicts a growth curve of *Acanthella cavernosa*, a tropical sponge, in a suspension culture using a medium in accordance with the present invention as described in Example 5.

Cells from the fourth passage are allowed to attach to plastic microcarriers for two hours in media with no gastropod plasma. The system is then stirred continuously, with fresh media containing 4% gastropod plasma being added in an attempt to keep the culture at a maximum growth rate, as illustrated in FIG. 2. The curve reflects a plot of the total number of cells times ten million versus days in suspension culture.

After 10 days the culture is harvested for qualitative analysis of antibiotic metabolites. This culture system is repeated several times, with the best results yielding 1.0 g of cells per 100 mL of media.

A sample of these cells is extracted with methanol and hexane. These extracts both demonstrate antibiotic properties, similar to extracts from the native sponge, against *Staphylococcus aureus* and *Bacillus subtilis*, in a standard natural product, antibiotic screening bioassay.

EXAMPLE 6

The marine nudibranch, *Aplysia californica*, is anesthetized with 8% $MgCl_2$ and then the albumin gland is surgically removed. The purple colored gland is minced with a razor, digested with trypsin/EDTA for one hour and then passed through a steel mesh. The resulting cells are placed in T75 flasks coated with gastropod plasma, fetal bovine plasma or bovine collagen type 1 (Col 1). The cells attached and grew best in the gastropod plasma flask. These cultures are expanded four times over 30 days, after which the confluent cultures are harvested and cryopreserved in freezing medium.

Thus it is shown that the present system provides for the long term culture of eukaryotic cells from marine invertebrates, and for the production of important metabolites from the cultures. Significantly, the system will function with cells from many different species of organisms, and will sustain commercially practical growth rates with concomitant metabolite production.

Furthermore, with appropriate supplementation, the present system provides for the long-term cryopreservation of such eukaryotic cells, while maintaining the viability and vigor of the cells when re-established in culture.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

I claim:

1. A system for the proliferation of marine invertebrate cells in in vitro culture comprising a culture of viable eukaryotic cells derived from at least one marine invertebrate organism in association with a culture medium which comprises components in the following approximate ranges: From 7.875 to 13.125 g/L of sodium, from 1.0 to 1.69 g/L of magnesium, from 14.25 to 23.8 g/L of chlorine, from 0.29 to 0.48 g/L of potassium, from 0.3 to 0.5 g/L of calcium, from 0.0225 to 0.0375 g/L of bromine, from 2.0 to 3.38 g/L of sulfate and from 10 to 100 mg/L of ascorbic acid.

2. The system according to claim 1 further comprising carbon sources.

3. The system according to claim 2 wherein said carbon sources are selected from the group consisting of galactose, mannose and fructose.

4. The system according to claim 1 further comprising from 30 to 300 mg/L of taurine.

5. A system for the cryopreservation of marine invertebrate cells or tissue comprising a culture of viable eukaryotic cells or tissue derived from at least one marine invertebrate organism in association with a culture medium which comprises components in the following approximate ranges: From 7.875 to 13.125 g/L of sodium, from 1.0 to 1.69 g/L of magnesium, from 14.25 to 23.8 g/L of chlorine, from 0.29 to 0.48 g/L of potassium, from 0.3 to 0.5 g/L of calcium, from 0.0225 to 0.0375 g/L of bromine, from 2.0 to 3.38 g/L of sulfate, from 5 to 20% by volume of gastropod plasma, approximately 7.5% by volume of DMSO and from 10 to 100 mg/L of ascorbic acid.

6. The system according to claim 5 further comprising carbon sources.

7. The system according to claim 6 wherein said carbon sources are selected from the group consisting of galactose, mannose and fructose.

8. The system according to claim 5 further comprising from 30 to 300 mg/L of taurine.

9. A method for producing metabolites from marine invertebrate cells in in vitro culture comprising:

providing a culture of viable eukaryotic cells derived from at least one marine invertebrate organism and capable of producing at least one metabolite of interest, said culture established in a culture medium which comprises components in the following approximate ranges: From 7.875 to 13.125 g/L of sodium, from 1.0 to 1.69 g/L of magnesium, from 14.25 to 23.8 g/L of chlorine, from 0.29 to 0.48 g/L of potassium, from 0.3 to 0.5 g/L of calcium, from 0.0225 to 0.0375 g/L of bromine, from 2.0 to 3.38 g/L of sulfate and from 10 to 100 mg/L of ascorbic acid; and culturing said cells for a time and under conditions sufficient to produce a desired quantity of said cell metabolite.

10. The method according to claim 9 wherein said culture medium further comprises carbon sources.

11. The method according to claim 10 wherein said carbon sources are selected from the group consisting of galactose, mannose and fructose.

12. The method according to claim 9 wherein said culture medium further comprises from 30 to 300 mg/L of taurine.

* * * * *